United States Patent
Beane et al.

(10) Patent No.: US 8,414,603 B2
(45) Date of Patent: Apr. 9, 2013

(54) APPLICATOR, ASSEMBLY, AND METHOD FOR CONNECTING AN INLET CONDUIT TO A HOLLOW ORGAN

(75) Inventors: Richard M. Beane, Hingham, MA (US); John W. Brown, Indianapolis, IN (US); James Alan Crunkleton, Weston, MA (US); James S. Gammie, Stevenson, MD (US); Joseph L. Smith, Concord, MA (US)

(73) Assignee: Correx, Inc., Waltham, MA (US)

( * ) Notice: Subject to any disclaimer, the term of this patent is extended or adjusted under 35 U.S.C. 154(b) by 80 days.

(21) Appl. No.: 12/238,406

(22) Filed: Sep. 25, 2008

(65) Prior Publication Data

US 2009/0082778 A1    Mar. 26, 2009

Related U.S. Application Data

(60) Provisional application No. 60/974,893, filed on Sep. 25, 2007.

(51) Int. Cl.
*A61F 2/04* (2006.01)

(52) U.S. Cl.
USPC ......................................................... 606/153

(58) Field of Classification Search .................. 606/153; 623/1.13, 1.15, 1.28, 1.3, 1.31, 23.64
See application file for complete search history.

(56) References Cited

U.S. PATENT DOCUMENTS

| | | |
|---|---|---|
| 4,118,806 A | 10/1978 | Porier et al. |
| 4,769,031 A | 9/1988 | McGough et al. |
| 4,794,928 A | 1/1989 | Kletschka |
| 5,500,014 A | 3/1996 | Quijano et al. |
| 5,843,088 A | 12/1998 | Barra et al. |

(Continued)

FOREIGN PATENT DOCUMENTS

| | | |
|---|---|---|
| WO | WO 82/01644 A | 5/1982 |
| WO | WO 93/00868 A | 1/1993 |
| WO | WO 2007/081418 | 7/2007 |

OTHER PUBLICATIONS

Sven Ivar Seldinger, Catheter replacement of the needle in percutaneous arteriography, 1953, pp. 368-376, vol. 39, Stockholm, Sweden.

*Primary Examiner* — Ryan Severson
(74) *Attorney, Agent, or Firm* — Pandiscio & Pandiscio

(57) ABSTRACT

The invention provides an applicator for forming a hole in a wall of a hollow organ and for connecting a hemostatic connection assembly to the hollow organ, wherein, when the hole is formed in the wall of the hollow organ, a first fluid seal exists between the hemostatic connection assembly and the wall of the hollow organ and a second fluid seal exists between the hemostatic connection assembly and the applicator, thereby minimizing fluid loss from the hollow organ. The invention further provides a hemostatic connection assembly for connecting an inlet conduit to a hollow organ, the hemostatic connection assembly comprising a organ wall connection portion, a cuff portion, an extension portion, and a seal ring portion, wherein, during the process of connecting the inlet conduit to the hollow organ, a first fluid seal exists between the organ wall connection portion and the wall of the hollow organ, and a second fluid seal exists between the hemostatic connection assembly and the inlet conduit, thereby minimizing fluid loss from the hollow organ. A method is also disclosed in which the applicator and hemostatic connection assemblies of the invention are used to connect an inlet conduit to a hollow organ.

14 Claims, 16 Drawing Sheets

U.S. PATENT DOCUMENTS

| | | |
|---|---|---|
| 6,083,237 A | 7/2000 | Huitema et al. |
| 6,146,325 A | 11/2000 | Lewis et al. |
| 6,266,550 B1 | 7/2001 | Selmon et al. |
| 6,409,739 B1 | 6/2002 | Nobles et al. |
| 6,416,527 B1 | 7/2002 | Berg et al. |
| 6,475,222 B1 | 11/2002 | Berg et al. |
| 6,712,831 B1 | 3/2004 | Kaplan et al. |
| 6,726,648 B2 | 4/2004 | Kaplon et al. |
| 6,863,677 B2 | 3/2005 | Breznock |
| 6,942,672 B2 | 9/2005 | Heilman et al. |
| 6,994,666 B2 | 2/2006 | Shannon et al. |
| 7,077,801 B2 | 7/2006 | Haverich |
| 7,510,561 B2 | 3/2009 | Beane et al. |
| 2001/0004675 A1 | 6/2001 | Woodard et al. |
| 2002/0045846 A1 | 4/2002 | Kaplon et al. |
| 2002/0082467 A1* | 6/2002 | Campbell ........................ 600/16 |
| 2002/0082614 A1 | 6/2002 | Logan et al. |
| 2002/0173808 A1 | 11/2002 | Houser et al. |
| 2003/0023255 A1 | 1/2003 | Miles et al. |
| 2003/0100816 A1 | 5/2003 | Siess |
| 2003/0130668 A1 | 7/2003 | Nieman et al. |
| 2004/0019375 A1* | 1/2004 | Casey et al. .................. 623/1.28 |
| 2004/0162608 A1 | 8/2004 | Haverich |
| 2005/0149093 A1 | 7/2005 | Pokorney |
| 2006/0036313 A1 | 2/2006 | Vassiliades |
| 2006/0089707 A1 | 4/2006 | Vassiliades et al. |
| 2007/0055357 A1 | 3/2007 | Pokorney et al. |

* cited by examiner

APPLICATOR, ASSEMBLY, AND METHOD FOR CONNECTING AN INLET CONDUIT TO A HOLLOW ORGAN

RELATED APPLICATION DATA

This application claims priority of U.S. Provisional Application Ser. No. 60/974,893, filed Sep. 25, 2007, which is hereby incorporated by reference in its entirety.

BACKGROUND OF THE INVENTION

1. Field of the Invention

The present invention relates to an applicator, assembly, and method for connecting an inlet conduit to a hollow organ, and more particularly, to a hemostatic connection assembly and inlet conduit connectable to the apex of a heart.

2. Description of the Related Art

As the average age of the United States population increases, so do the instances of aortic stenosis. An alternative approach to the conventional surgical replacement of the stenotic aortic valve involves the use of an apicoaortic conduit. In this approach, the native aortic valve is not removed, and a prosthetic valve is implanted in a parallel flow arrangement. A connection conduit (or tube) connects the apex of the heart to the descending aorta. Somewhere along this conduit, the prosthetic valve is interposed. Thus, blood leaves the heart through the apex and travels through the conduit (with valve) to the descending aorta.

Until recently, surgical procedures to implant an apicoaortic conduit have included a single, long incision, such as in the 6th intercostal space, to expose the heart and allow retraction of the lungs to expose the descending aorta. Recognizing the potential for broader scale use of the apicoaortic conduit for aortic valve replacement, some surgeons are now attempting to use smaller incisions and are requesting development of surgical tools for a minimally invasive procedure.

A typical implantation procedure for an apicoaortic conduit is described as follows. The patient placed is on the operating table in the supine position. Anesthesia is induced, and the patient is intubated with a double-lumen endotracheal tube, which facilitates one-lung ventilation and allows the surgeon to work within the left chest. The patient is positioned with the left side up (90 degrees). The pelvis is rotated about 45 degrees, such that the femoral vessels are accessible. An incision is made over the femoral vessels, and the common femoral artery and vein are dissected out. Heparin is administered. Purse string sutures are placed in the femoral artery and vein. The artery is cannulated first, needle is inserted into the artery, and a guide wire is then inserted. Transesophageal echo is used to ascertain that the wire is in the descending aorta. Once this is confirmed, an arterial cannula is inserted over the wire, into the artery using the Seldinger technique (Sven-Ivar Seldinger: Catheter replacement of the needle in percutaneous arteriography (a new technique) Acta Radiologica, Stockholm, 1953, 39:368-376). The arterial cannula is typically 19 or 21 French. Once inserted, the purse string sutures are snugged down over tourniquets. A similar procedure is followed for the femoral vein. The venous cannula is usually a few French larger than the arterial cannula. Once both vein and artery are cannulated, the cannulae are connected to the cardiopulmonary bypass, and the capability to initiate cardiopulmonary bypass at any time is present.

A 1 cm incision is made in approximately the 7th interspace in the posterior axillary line, a videoscope (10 mm diameter) is inserted, and the left chest contents viewed. The location of the apex of the heart is determined, and the light from the scope used to transilluminate the chest wall, which this allows precise localization of the incision. The incision is then performed, which is essentially an anterior thoracotomy, typically in the 6th interspace. Recent incisions have been about 10 cm long, but are expected to become smaller and smaller with time. A retractor is inserted and the wound opened gently. A lung retractor is used to move the (deflated) left lung cephalad. A pledgeted suture is placed on the dome of the diaphragm and positioned to pull the diaphragm toward the feet (out of the way). The pericardium is incised about the apex of the heart, and the apex is freed up and clearly identified.

Currently available commercial devices used to construct the implantable apicoaortic conduit include the Hancock valved conduit and Hancock apical connector (from Medtronic, Inc. 710 Medtronic Parkway, Minneapolis, Minn., 55432-5604 United States), which are sewn together to form the complete implant assembly. The assembly is brought to the field, and a measurement made from the apex of the heart to the descending aorta. The assembly is trimmed appropriately. A partial-occluding clamp is then placed on the descending aorta, and the aorta opened with a knife and scissors. The outflow end of the conduit is then sutured to the descending aorta using 4-0 prolene suture, in a running fashion. Once this is complete, the clamp is removed and the anastomosis checked for hemostasis. Blood is contained by the presence of the Hancock valve.

The most technically challenging aspect of implanting the apicoaortic conduit is placement of the apical connector, which has historically been performed in a two-step process by first cutting and removing a cylindrical tissue plug from the apex and then inserting the apical connector into the formed hole. This two-step process creates potential for significant blood loss after the hole is formed and before the apical connector is inserted. Placement of the apical connector has historically been performed as follows. The apical connector is placed on the apex, and a marker is used to trace the circular outline of the connector on the apex, in the planned location of insertion. Four large pledgeted sutures (mattress sutures) of 2-0 prolene are placed, one in each quadrant surrounding the marked circle. The sutures are then brought through the sewing ring of the apical connector. A stab wound is made in the apex in the center of the circle, and a tonsil clamp is used to poke a hole into the ventricle. Cardiopulmonary bypass is typically initiated at this point. A Foley catheter is inserted into the ventricle, and the balloon expanded. A cork borer is then used to cut out a plug from the apex. The apical connector is then parachuted down into position. A rotary motion is necessary to get the connector to seat in the hole. The four quadrant sutures are tied, and hemostasis is checked. If there is a concern regarding hemostasis, additional sutures are placed. The retractor is removed, chest tubes are placed, and the wound is closed.

An improved alternative method and device for placement of the apical connector is described in U.S. patent application Ser. No. 11/086,577, (U.S. Patent Application Publication No. 20050251187), which is hereby incorporated by reference in its entirety. The '577 application describes an applicator and connector conduit (referred to interchangeably as the apical connector) adapted for cutting and removing a cylindrical tissue plug from the apex while the connector conduit is being inserted into the formed hole. This device allows placement of the connector conduit without cardiopulmonary bypass and with minimal blood loss.

The '577 application discloses an apparatus and method for connecting a first conduit to the heart without the need for cardiopulmonary bypass. The first conduit may then be attached to a second conduit that has a prosthetic device interposed. The second conduit may be connected to the aorta prior to the first conduit being attached to the heart. The prosthetic device may be a prosthetic valve or a pump, for example. The apparatus includes an implantable connector with first conduit component, a retractor expansion component, a coring component, and a pushing component. The retractor expansion component is slide-ably coupled to the coring component. The retractor expansion component serves to seat against and separate the inside apical wall of the left ventricle so that the coring component may cut cleanly through the myocardium to form a tissue plug without leaving any hanging attachments to the inside walls. By remaining seated against the inside wall of the hollow organ, the retractor expansion component follows the tissue plug into the coring component. The surgeon applies force and rotary motion to the pushing component sufficient to cut the tissue plug and implant the prosthetic component.

Prior art FIGS. 1A and 1B are copies of FIGS. 10A and 10B of the '577 application, presented herein for illustrative purposes. As described in the '577 application, hemostasis is achieved during implantation of the conduit by substantially blocking leak paths through and around the connector conduit.

Referring to the figures, the connector conduit has a structural frame 120 defining a rigid portion, which may be constructed from a single material or a combination of materials. The structural frame 120 includes a tapered leading edge 110 designed to reduce the effort needed to push the connector through the heart wall located at one end of a cage section 120 and a bend portion 140 that is normally biased into a bent configuration. During use, cage 120 resides primarily within the heart wall, so it must be constructed so as to be rigid enough to not collapse due to radial forces exerted by the heart wall. The cage 120 may include cage slots 121. The cage slots 121 allow the passage of thread to secure the conduit or the sewing flange. A holder 130 is formed at one end of cage 120 and may be used to grasp the connector during implantation. Holder 130 may have a slot-and-key configuration with the applicator, and may utilize holder slots 431. In a preferred configuration, the holder 130 relies upon both a slot-and-key and a tight friction fit to lock the holder 130 relative to the applicator.

Bend portion 140 includes circular rings 141 and a curved spine 142. The circular rings 141 prevent radial collapse of the conduit, and the curved spine 142 holds the conduit in a preferred shape to direct blood flow from the heart to the aorta. The curved spine 142 may be at the outer radius of bend portion 140 (as shown) or at the inner radius of the flexible bend. As an alternative, flexible bend 140 may include two curved spines at the mean radius. As another alternative, the structural frame 120 could include circular rings 141 without curved spine 142. As another alternative, a modified coil spring in the shape of a preferred bend could be used instead of circular rings 141 and curved spine 142. Properties of the coil spring would be chosen to prevent radial collapse and to provide appropriate stiffness of the curved position.

As is described in the '577 application, the leak path through the lumen of the connector conduit is substantially blocked by the applicator. The leak path around the connector conduit is substantially blocked by a tight interference fit between the outer surface of the fabric-covered cage 120 and the cut surface of the hole in the apex. This interference fit is the result of the cutting element of the applicator having a smaller diameter than the outer surface of the fabric-covered cage 120. For example, the outer diameter of the cutting element could be 0.7 in and the outer diameter of the fabric-covered cage could be 0.9 in.

Once the connector conduit is implanted and the applicator is removed, the leak path around the connector conduit is blocked to achieve hemostasis in two ways. First, the interference fit remains intact. Second, a sealing surface is formed by tightly suturing the sewing flange to the apex. These sutures also prevent the connector conduit from being pushed out of the hole by the blood pressure in the left ventricle.

Apical connectors consisting of an inlet cannula and sewing cuff are currently used in other applications, such as left ventricular assist devices. For example, Ventricular Assist Devices, referred to as VADs or LVADs, are enclosed pump devices used to augment the pumping capability of a damaged or failing heart. Such devices often have an inlet cannula pre-attached to the body of the device and thus, cannot be preloaded onto the applicator described in the '577 application.

An example of an existing inlet cannula is the Thoratec HeartMate II LVAD's inlet cannulae (Thoratec Corporation, 6101 Stoneridge Drive, Pleasanton, Calif. 94588) which, with the patients on cardiopulmonary bypass, are currently implanted as described as follows. A trocar (or cutting element) is used to cut a hole in the apex of the heart. Several sutures are then placed through the sewing ring of the sewing cuff and through the apex. After the sutures are pulled tight and knots are tied, the sewing cuff is positioned in place. The inlet extension of the inlet cannula is inserted through the sewing cuff and through the hole in the apex until the inlet extension is at the desired position. The position of the inlet extension within the sewing cuff is set and hemostasis is achieved by tightly tying the long suture around the flexible tube of the sewing cuff.

As discussed above, the '577 application describes the insertion of a connector conduit into a hollow organ. Referring again to prior art FIGS. 1A and 1B, as well as prior art FIG. 2, which is a copy of FIG. 14 of the '577 application, the connector conduit includes a cage of structural frame 120 and sewing flange 170. The cage and sewing flange 170 are rigidly connected by a fabric covering. The connector conduit described in the '577 application may be used instead of the inlet cannula on such medical devices as LVADs. The fabric-covered cage is analogous to an LVAD inlet cannula and sewing flange 170 is analogous to an LVAD sewing ring. It is important to note that the inlet cannula and sewing cuff are rigidly connected (thereby setting position and providing hemostasis) only after a long suture is tied tightly around the flexible tube of the sewing cuff.

More specifically, FIG. 2 shows a cross-section of a connector conduit 100 that includes a rigid portion defined by structural frame 120 with bend portion 140, and a flexible portion defined by conduit 160. The rigid portion also includes outer fabric 161, and sewing flange 170. Orientation marks (not shown) may be included on the conduit 160 or outer fabric 161. Conduit 160 may be a pleated vascular graft constructed of woven Dacron. Outer fabric 161 could be a knitted Dacron fabric material that stretches to accommodate contours of the structural frame 120. Sewing flange 170 could be constructed of a soft silicone rubber, for example, to allow easy passage of a needle when fastening sewing flange (or sewing ring) 170 to the outer surface of the heart. To allow visualization on x-ray, for example, the sewing flange could be made radiopaque, such as by mixing barium sulfate into the silicone rubber. The sewing flange may have a cloth covering such as that used for outer fabric 161. Alternatively, the sewing flange 170 may consist entirely of folded cloth. The components of the connector conduit 100 may be fastened together as needed, such as with thread.

U.S. Pat. No. 6,942,672 to Heilman et al. describes an apparatus and method for attaching a conduit to the heart, such as a conduit for connection to an implantable blood pump, or to a blood vessel, as in a heart bypass graft, without the need for a cardiopulmonary bypass. The apparatus can include an enclosure attachable to the heart and having sealed within the enclosure at least part of a coring tool and one end of the conduit which will be attached to the heart. A heart attachment member can be affixed to the enclosure for facilitating attachment of the apparatus to the heart and the coring tool can have a cutting member and a member for holding the tissue to be cut from the heart. All air can be evacuated from the enclosure prior to cutting tissue from the heart and attachment of the conduit.

However, with a system such as that disclosed in the '672 patent, a major difficulty is that, during use, the moment that the coring means penetrates the heart wall, the action of the heart will cause blood to enter the enclosure and either fills it if it is evacuated or mixes with the saline if it is prefilled. In either case, the opacity of the blood or blood saline mixture will obscure further action of the coring means and make accurate placement of the conduit difficult. In addition, because the heart is beating the flexible enclosure will be in constant pulsatile motion further complicating accurate use of the enclosed tools. From the description and the figures in the patent, the enclosure needs to be somewhat large to accommodate the proper movement of the tools and therefore will contain a large amount of blood or blood and saline mixture. If the enclosure is accidentally breached, for example by a sharp edge of the coring tool or the implant, a large amount blood immediately floods the operating field. Since no other means beyond the enclosure is provided to limit flow of blood, the beating heart will pump out a significant additional amount of blood before the field is cleared and the bleeding is controlled. This could result in significantly negative outcomes, including death, for the patient.

SUMMARY OF THE INVENTION

The current invention is intended to provide another alternative for placement of an inlet conduit. As described herein, the apical connector consists of two separate components that are assembled during implantation. The first component is an inlet conduit, or inlet cannula, which is substantially a rigid or semi-rigid tube that extends through the wall of the heart. For example, the inlet conduit may consist of a cloth-covered stent. As another example, the inlet conduit could be a titanium tube with a portion of its surface area having sintered titanium. The second component is a hemostatic connection assembly, which may be a sewing cuff, for example.

Thus, the invention relates to an applicator for forming a hole in a wall of a hollow organ and for connecting a hemostatic connection assembly to the hollow organ. The applicator preferably includes a hole forming element adapted to form a hole in the wall of the organ, the hole forming element including a cutting element on a distal end thereof, a retractor element disposed at least partially within the hole forming element, the retractor element comprising a tip at a distal end thereof adapted to penetrate the wall of the hollow organ, and an expansion element positioned near the distal end, the expansion element having a plurality of expansion states, a sequencing means for coordinating expansion of the expansion element between the expansion states based on the position of the retractor element relative to the hole forming element, and a mounting element coupled to the hole forming element, the mounting element being configured to support the hemostatic connection assembly. When the hole is formed in the wall of the hollow organ, the hemostatic connection assembly is positioned on the mounting element and connected to the hollow organ such that a first fluid seal exists between the hemostatic connection assembly and the wall of the hollow organ and a second fluid seal exists between the hemostatic connection assembly and the applicator, thereby minimizing fluid loss from the hollow organ.

The hemostatic connection assembly preferably includes an organ wall connection portion, a cuff portion, and an extension portion, and the mounting element preferably includes a cuff support portion configured to support the cuff portion of the hemostatic connection assembly, and an extension support portion configured to support the extension portion of the hemostatic connection assembly.

In this embodiment, the cutting element may be a cutting blade, and the hollow organ is preferably a beating heart. Moreover, the plurality of expansion states may include an unexpanded state, a fully expanded state, and at least one partially expanded state, and the expansion element may be a balloon, which, when substantially fully expanded, is in the shape of a circular toroid. The cuff support portion may also have an outer diameter that is substantially equal to an inner diameter of the cuff portion.

In addition, the applicator may further comprise an occluding means for preventing excessive fluid loss through the applicator such that the hollow organ remains at substantially normal physiological pressures while the hole is being formed in the hollow organ. The occluding means may comprise an outer diameter of at least a portion of the retractor element and an inner diameter of at least a portion of the hole forming element. The mounting element may further comprise a stop portion adapted to restrict the travel distance of the retractor element into the hollow organ.

Furthermore, the sequencing means may comprise a means for expanding the expansion element between the plurality of expansion states. Exemplary means for expanding may include a syringe in fluid communication with the expansion element or a cylinder having a piston slideable therein and coupled to the expansion element. The sequencing means may also comprise a means for moving the retractor element relative to the hole forming element whereby the expansion element is moved from a position distally outside of the hole forming element to a position at least partially disposed within the hole forming element. In this embodiment, the retractor element may include a cylinder portion and a retractor mounting portion extending from a distal end of the cylinder portion, the expansion element being disposed on the retractor mounting portion, and wherein the sequencing means comprises a sequencing bolt coupled to the means for expanding.

The sequencing means may also comprise a means for causing the elements to assume the following states in seriatim, a) a first state where the retractor element is locked in a fully extended position relative to the hole forming element with the expansion element in the unexpanded state, b) a second state in which the expansion element is in the fully expanded state and the expansion element moves toward the hole forming element, c) a third state in which the hole has been formed, and d) a fourth state in which the expansion element is in the partially expanded state and the expansion element is moved to be at least partially disposed in the hole forming element.

The invention further relates to a hemostatic connection assembly for connecting an inlet conduit to a hollow organ.

The hemostatic connection assembly preferably comprises a organ wall connection portion adapted to connect to a wall of a hollow organ, a cuff portion connected to the wall connection portion, the cuff portion being adapted to support the inlet conduit during insertion of the inlet conduit through the wall of the hollow organ, an extension portion connected to the cuff portion, the extension portion being extendible from a compressed state to an extended state, and a seal ring portion connected to the extension portion, the seal ring portion being adapted to connect to a portion of the inlet conduit. During the process of connecting the inlet conduit to the hollow organ, a first fluid seal preferably exists between the organ wall connection portion and the wall of the hollow organ, and a second fluid seal preferably exists between the hemostatic connection assembly and the inlet conduit, thereby minimizing fluid loss from the hollow organ.

The inlet conduit may be an inlet cannula, and the hollow organ may be a beating heart. In addition, the organ wall connection portion may be adapted to be connected to the wall of the hollow organ using sutures, adhesives, staples, or other known means.

The hemostatic connection assembly may also be an integral component or may include a plurality of separate pieces. For example, the organ wall connection portion may be integral or separate from the cuff portion, the cuff portion may be integral or separate from the extension portion, and the extension portion may be integral or separate from the seal ring portion. The cuff portion may also be removably connected to the extension portion.

The cuff portion is also preferably substantially rigid, while the extension portion may be formed of a flexible material, such as polyurethane, woven polyester, and the like. The extension portion may also include at least one convolution.

The invention further provides a method of connecting an inlet conduit to a hollow organ using a hemostatic connection assembly. The method preferably comprises the steps of positioning the hemostatic connection assembly on the applicator for forming a hole in a wall of a hollow organ such that a fluid seal is formed between the hemostatic connection assembly and the applicator, connecting the hemostatic connection assembly to a wall of the hollow organ such that a fluid seal is formed between the hemostatic connection assembly and the wall of the hollow organ, forming a hole in the wall of the hollow organ using the applicator, withdrawing the applicator from the hole formed in the wall of the hollow organ while maintaining the fluid seal between the hemostatic connection assembly and the applicator, occluding the hemostatic connection assembly to form a fluid seal, detaching the applicator from the hemostatic connection assembly while maintaining the fluid seal formed by the occlusion of the hemostatic connection assembly, inserting an inlet conduit into the hemostatic connection assembly such that a fluid seal is formed between the hemostatic connection assembly and the inlet conduit, removing the occlusion of the hemostatic connection assembly, and inserting the inlet conduit into the hole formed in the wall of the hollow organ.

The method may further comprise the steps of forming a further fluid seal between the inlet conduit and the hemostatic connection assembly such that a predetermined portion of the hemostatic connection assembly can be removed without excessive fluid loss, and removing the predetermined portion of the hemostatic connection assembly.

As described above, the hemostatic connection assembly used in the method may comprise a organ wall connection portion adapted to connect to the wall of the hollow organ, a cuff portion connected to the wall connection portion, the cuff portion being adapted to support the inlet conduit during insertion of the inlet conduit through the wall of the hollow organ, an extension portion connected to the cuff portion, the extension portion being extendible from a compressed state to an extended state, and a seal ring portion connected to the extension portion, the seal ring portion being adapted to connect to a portion of the inlet conduit, wherein, during the process of connecting the inlet conduit to the hollow organ, a fluid seal exists between the organ wall connection portion and the wall of the hollow organ, and a fluid seal exists between the hemostatic connection assembly and the inlet conduit, thereby minimizing fluid loss from the hollow organ. The inlet conduit may also be an inlet cannula.

As described above, the applicator used in the method may comprise a hole forming element adapted to form the hole in the wall of the organ, the hole forming element including a cutting element on a distal end thereof, a retractor element disposed at least partially within the hole forming element, the retractor element comprising a tip at a distal end thereof adapted to penetrate the wall of the hollow organ, and an expansion element positioned near the distal end, the expansion element having a plurality of expansion states, a sequencing means for coordinating expansion of the expansion element between the expansion states based on the position of the retractor element relative to the hole forming element, and a mounting element coupled to the hole forming element, the mounting element being configured to support the hemostatic connection assembly, wherein, when the hole is formed in the wall of the hollow organ, a fluid seal exists between the hemostatic connection assembly and the wall of the hollow organ, and a fluid seal exists between the hemostatic connection assembly and the applicator, thereby minimizing fluid loss from the hollow organ.

In this embodiment, the fluid seal between the hemostatic connection assembly and the applicator may be formed by the positioning of the hemostatic connection assembly relative to the mounting element. Similarly, the fluid seal between the hemostatic connection assembly and the wall of the hollow organ may be formed by sutures or other means of connecting the hemostatic connection assembly to the wall of the hollow organ. Furthermore, the fluid seal between the hemostatic connection assembly and the inlet conduit may be formed by positioning a seal ring portion of the hemostatic connection assembly around the inlet conduit, by using sutures or umbilical tape, or by any other suitable means.

Also, the occlusion of the hemostatic connection assembly may be caused by any known means, for example, by a compression of the hemostatic connection assembly, such as by clamping, or through the use of an inflatable device, such as a balloon. The inlet conduit may be substantially rigid or flexible.

According to the invention and the exemplary embodiments described herein, the fluid seals between the wall of the hollow organ, the hemostatic connection assembly, the applicator, and the inlet conduit prevent excessive fluid leakage during the installation of the inlet conduit into the hollow organ.

As will be recognized by a person of ordinary skill in the art, the applicator or the invention described herein is a modified version of the applicator described in the '577 application which allows implantation of an inlet conduit, such as an inlet cannula, without cardiopulmonary bypass.

The applicator of the invention allows for the hemostatic connection assembly and inlet conduit to be installed to the hollow organ separately. Specifically, after the hemostatic connection assembly is installed, the applicator is removed, and the inlet conduit is inserted into the hemostatic connection assembly and the hole in the wall of the hollow organ. Fluid seals are maintained throughout the procedure to prevent excessive fluid loss.

Providing hemostasis throughout implantation of the inlet conduit without cardiopulmonary bypass requires creating a series of hemostatic (i.e. fluid) seals. For example, four states with defined hemostatic seals are needed.

State 1: After the hole is formed in the wall of the organ by the applicator, three fluid seals are desired, including a fluid seal between the hemostatic connection assembly and the wall of the hollow organ, a fluid seal between the hemostatic connection assembly and the applicator, and an occlusion to prevent fluid loss through the applicator itself.

State 2: After the applicator has been removed from the hemostatic connection assembly, two fluid seals are desired, including the fluid seal between the hemostatic connection assembly and the wall of the hollow organ and the occlusion of the hemostatic connection assembly.

State 3: After the occlusion of the hemostatic connection assembly is removed, three fluid seals are desired, including the fluid seal between the hemostatic connection assembly and the wall of the hollow organ, a fluid seal between the hemostatic connection assembly and the inlet conduit, and an occlusion of the inlet conduit by some other means, for example, by a valve or other device downstream of the inlet conduit, for example, a Ventricular Assist Device.

State 4: After a portion of the hemostatic connection assembly is (optionally) removed, thereby finalizing the installation of the inlet conduit, two fluid seals are desired, including the fluid seal between the hemostatic connection assembly and the wall of the hollow organ, and a further fluid seal between the remaining portion of the hemostatic connection assembly and the inlet conduit.

BRIEF DESCRIPTION OF THE DRAWINGS

Prior art

Prior art

DETAILED DESCRIPTION OF THE INVENTION

Figure 1A:
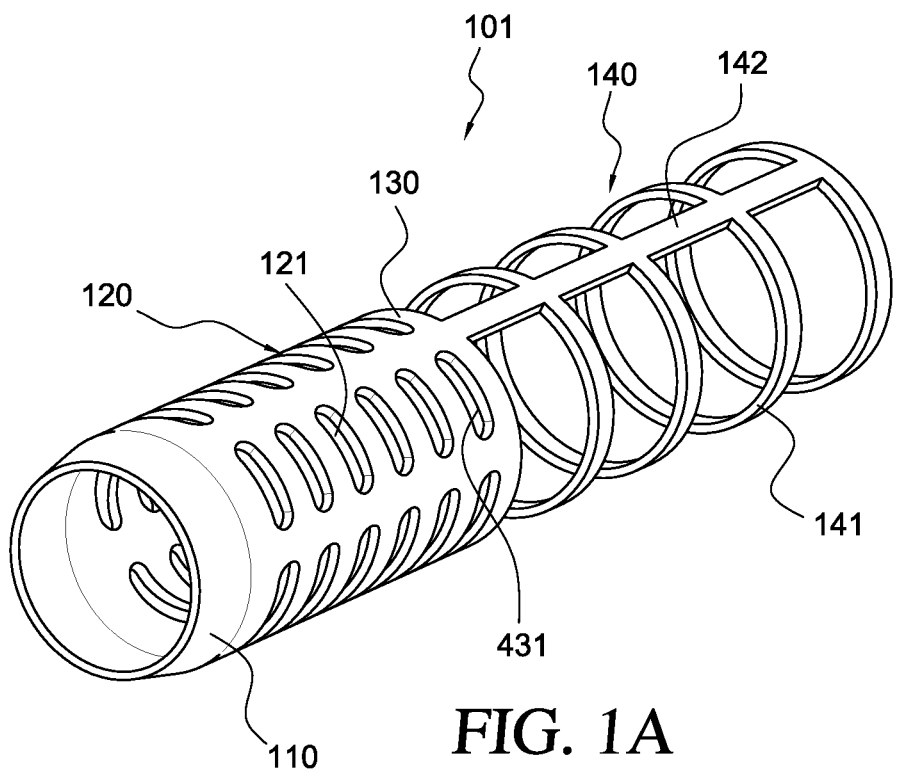
FIGS. 1A and 1B are copies of FIGS. 10A and 10B of the '577 application showing an exemplary connector conduit structural frame.
Figure 1B:
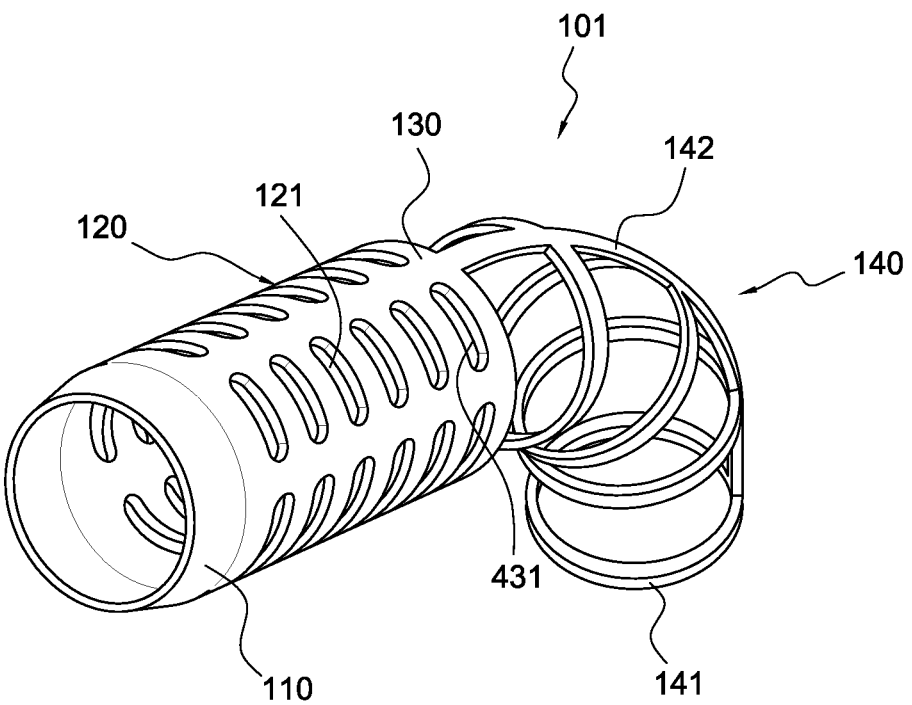
Figure 2:
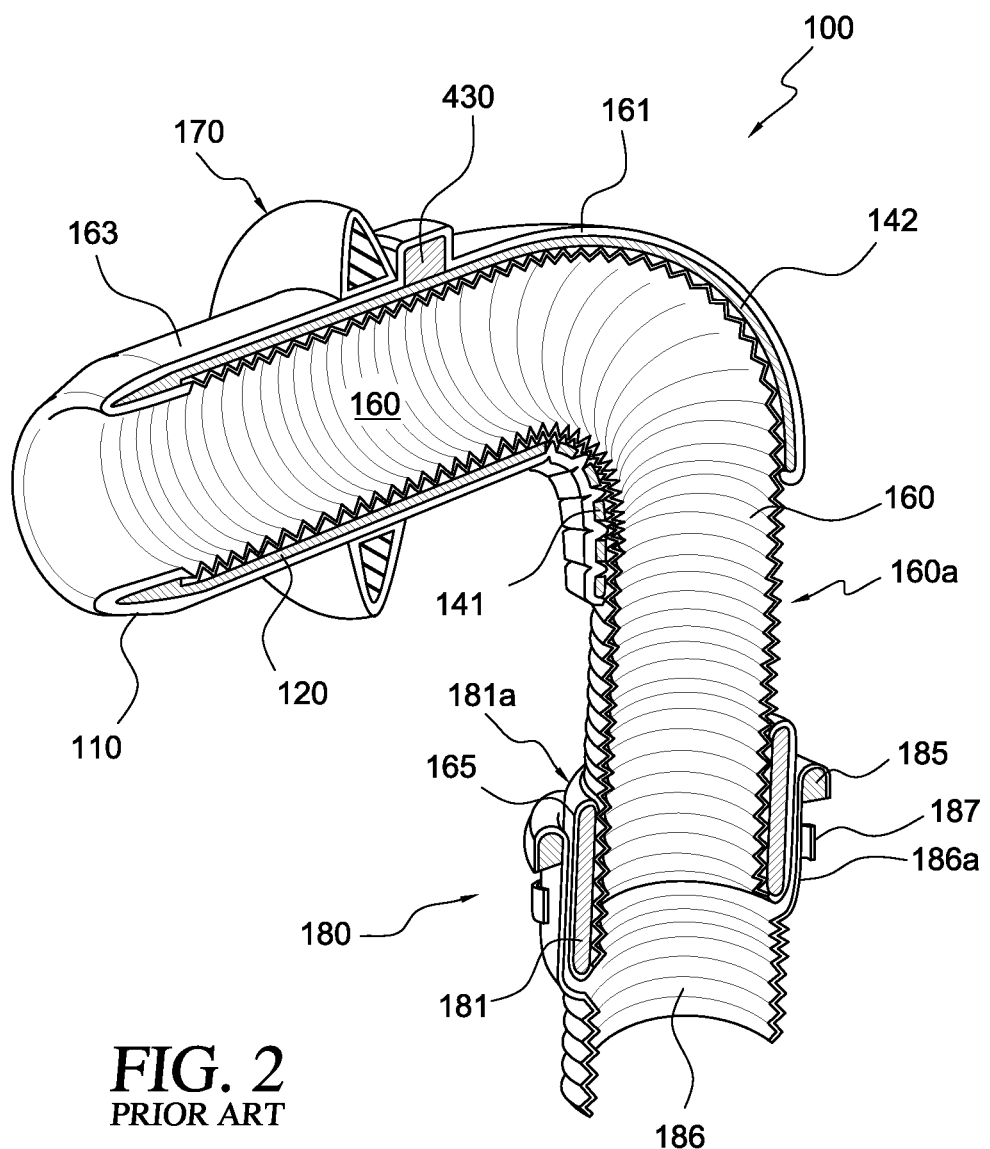
FIG. 2 is a copy of FIG. 14 of the '577 application showing an exemplary connector conduit in cross-section containing the structural frame.
Figure 3A:
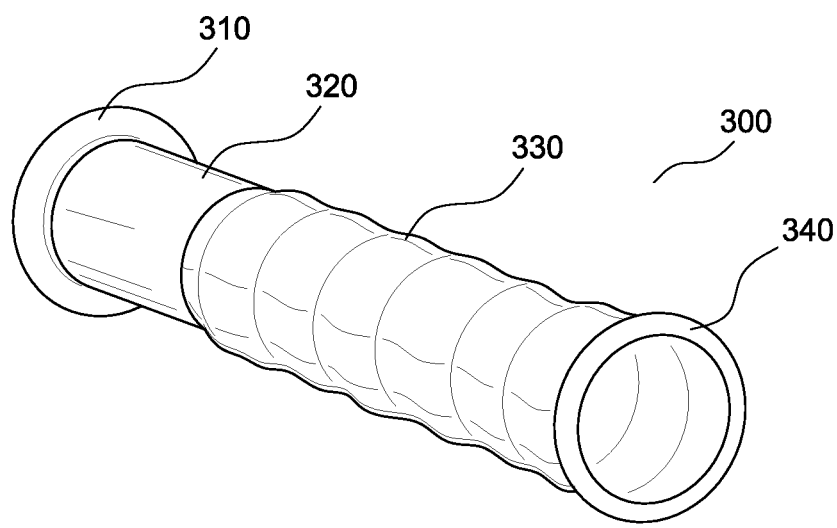
FIGS. 3A and 3B illustrate an exemplary hemostatic connection assembly of the invention.
Figure 3B:
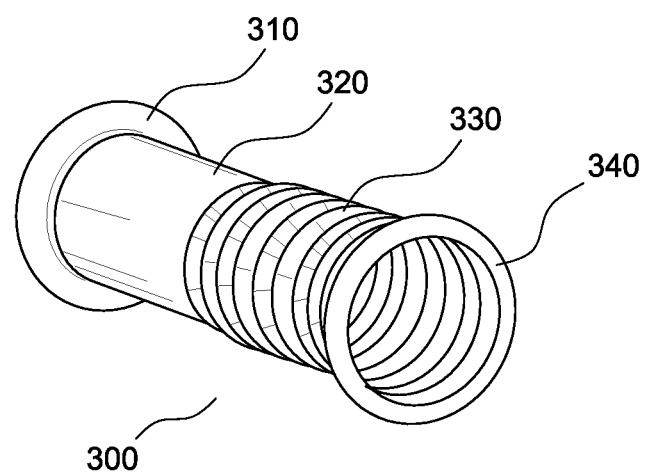

Referring now to the figures, FIGS. 3A and 3B illustrate an exemplary hemostatic connection assembly of the invention. Hemostatic connection assembly 300 preferably comprises an organ wall connection portion 310 adapted to connect to a wall of a hollow organ, a cuff portion 320, an extension portion 330, and a seal ring portion 340. FIG. 3A shows hemostatic connection assembly 300 with extension portion 330 in an extended state, and FIG. 3B shows hemostatic connection assembly 300 with extension portion 330 in a collapsed or compressed state.

On one end of hemostatic connection assembly 300, extension portion 330 (which may be referred to as a sewing cuff extension herein) is connected to cuff portion 320 (which may be referred to as a sewing cuff herein). The connection between cuff portion 320 and extension portion 330 is preferably a removable connection. The connection between extension portion 330 and cuff portion 320 may be of any suitable type, such as an adhesive or by a radio frequency weld. On the other end, extension portion 330 may include a seal ring portion 340, which is used to form a hemostatic, fluid seal with one or both of the inlet conduit or the applicator, depending on the situation.

While the components of hemostatic connection assembly 300 shown in the figures to be separate components, it should be understood that the various components may also be formed integrally. For example, organ wall connection portion 310 may be integral or separate from cuff portion 320, cuff portion 320 may be integral or separate from extension portion 330, and extension portion 330 may be integral or separate from seal ring portion 340.

Cuff portion 320 may be formed of any suitable material. In addition, cuff portion 320 is preferably substantially rigid. In contrast, extension portion 330 is preferably formed of a flexible material which allows for the necessary expansion and contraction of extension portion 330. Preferably, extension portion 330 includes a thin-walled flexible tube that can be 1) clamped or otherwise occluded to prevent blood flow, 2) collapsed predictably to shorten its axial length, and 3) twisted to allow rotation of applicator 400 relative to hemostatic connection assembly 300, as needed. The flexible tube could be made of polyurethane, for example, and have a wall thickness of 0.002 in to 0.01 in, for example. The flexible tube could also include have convolutions, as illustrated, which allow the tube to be shortened axially without creating additional creases in the tube. FIG. 3B shows extension portion 330 collapsed in the axial direction.

Alternatively, extension portion 330 may not include convolutions. For example, extension portion 330 may include a thin-walled tube (See FIG. 13). Rather than using convolutions to allow extension portion 330 to shorten its axial length, extension portion 330 may fold over itself to shorten axially (intussusception), with the folded portion extending over a portion of inlet conduit 500. Once inlet conduit 500 is in its final position and secured within the hollow organ (or apex), extension portion 330 may be removed, such as by tearing or cutting off extension portion 330.

Figure 4:
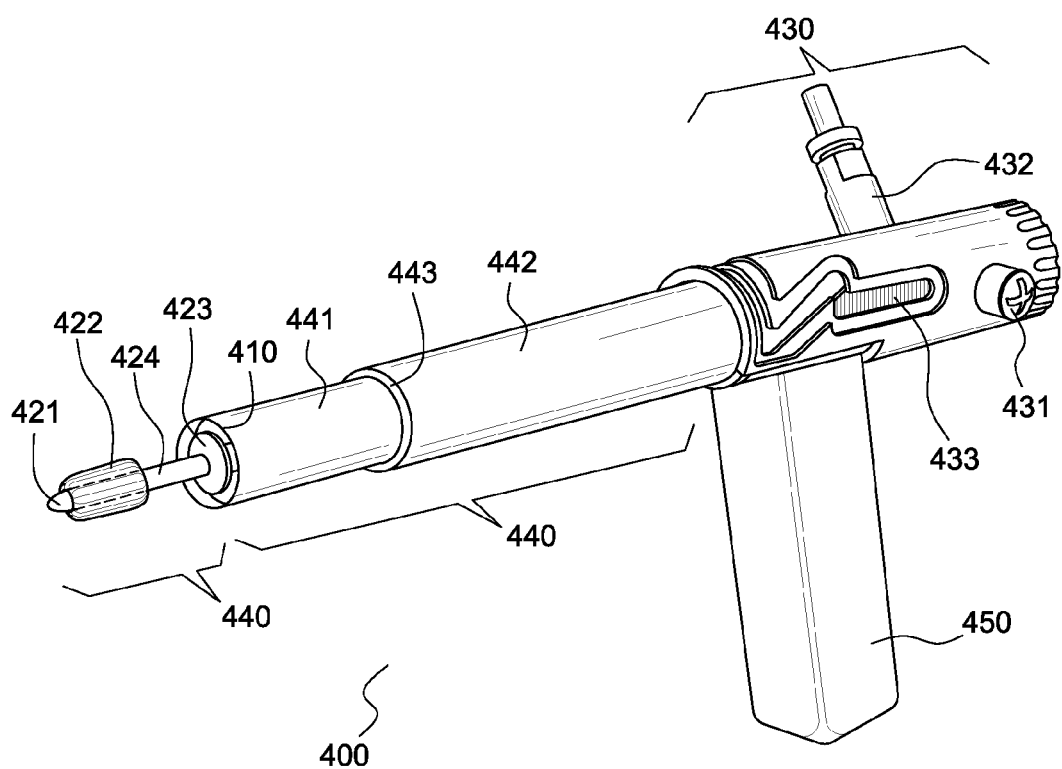
FIG. 4. illustrates an applicator of the invention.
Figure 5:
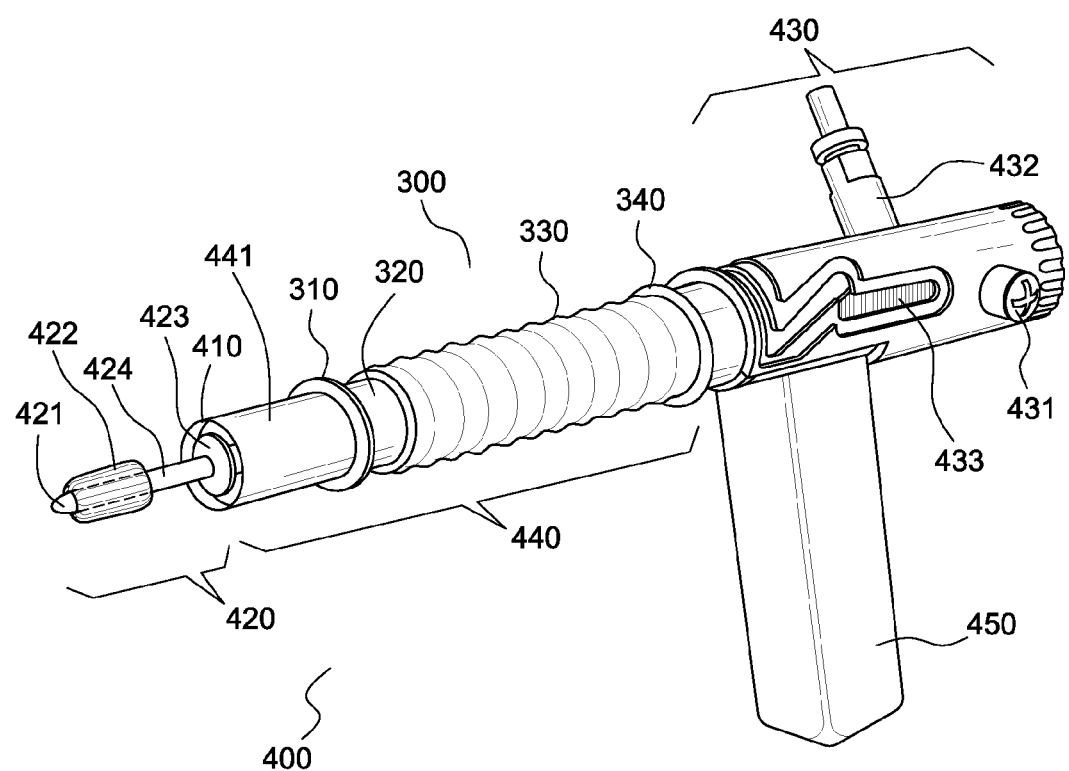
FIG. 5. illustrates an embodiment of the invention in which a hemostatic connection assembly is positioned on an applicator.

As is shown in FIGS. 4 and 5, hemostatic connection assembly 300 is positioned on an applicator 400 for use during the procedure, which is used to form a hole in a wall of a hollow organ and for connecting hemostatic connection assembly 300 to the hollow organ. Applicator 400 preferably includes a hole forming element 410, a retractor element 420, a sequencing means 430, and a mounting element 440. Hole forming element 410 is adapted to form a hole in the wall of the organ. Accordingly, hole forming element 410 preferably includes a cutting element on a distal end thereof, such as a cutting blade. Retractor element 420 is preferably disposed at least partially within hole forming element 410, and includes a tip 421 at a distal end thereof adapted to penetrate the wall of the hollow organ and an expansion element 422 positioned near the distal end. Sequencing means 430 is used to coordinating expansion of expansion element 422 between a plurality of expansion states based on the position of retractor element 420 relative to hole forming element 410.

Mounting element 440 is coupled to hole forming element 410, and is configured to support hemostatic connection assembly 300. Specifically, mounting element 440 preferably includes a cuff support portion 441 configured to support cuff portion 320 of hemostatic connection assembly 300, and an extension support portion 442 configured to support extension portion 330 of hemostatic connection assembly 300. The annular gaps between mounting element 400 and extension portion 330 provide flow resistance to substantially prevent blood loss before extension portion 330 is occluded. Seal ring portion 340 may also be mounted onto a flange on mounting element 440 to substantially eliminate blood loss. Transition from the smaller diameter to the larger diameter on mounting element 440 serves as a stop 443 to limit axial slide of cuff portion 320 on mounting element 340.

In an alternate configuration, mounting element 440 may have a constant diameter that fits within the cuff portion 320, and seal ring portion 340 may be placed snugly onto a sliding sleeve (not shown) on mounting element 440. The sliding sleeve would be shaped such that a small annular gap exists between the sliding sleeve and mounting element 440, thereby creating a fluid seal between seal ring portion 340 and mounting element 440. Seal ring portion 340 may be removed from the sliding sleeve after the extension portion 330 is occluded. The axial slide of cuff portion 320 on mounting element 440 can be limited by placing a visual indicator on mounting element 440, such as an indicator mark, or by positioning a flange on mounting element 440 that would prevent the sliding sleeve from sliding too far along mounting element 440 after the hole is cut in hollow organ 200.

The '577 application, which is incorporated by reference, describes the general operation of an applicator fundamentally similar to the one described herein.

Applicator 400 may also include an occluding means for preventing excessive fluid loss through applicator 400 such that the hollow organ remains at substantially normal physiological pressures while the hole is being formed in the hollow organ. The occluding means may include, for example, an outer diameter of at least a portion of retractor element 420 and an inner diameter of at least a portion of hole forming element 410.

Retractor element 420 may include a disk portion 423 and a retractor mounting portion 424 extending from a distal end of disk portion 423, expansion element 422 being disposed on retractor mounting portion 424. Hole forming element 410 is preferably made with dimensions (e.g., diameters, cutting edge tapers, sharpness) appropriate to fit inlet conduit 500, or the inlet cannula. In operation, hemostatic connection assembly 300 is connected to the wall of hollow organ 200 before applicator 400 is pushed and rotated to cut the tissue plug. Thus, applicator 400 must be able to rotate and move axially within cuff portion 320 and extension portion 330 while the hole is being cut in the hollow organ. A lubricant on the surface of mounting element 440 may be needed to reduce friction and sticking within cuff portion 320. A pushing element may be used to replace stop 443 shown in FIG. 4, and either a stop or a component similar to the pushing element is needed to limit axial motion of cuff portion 320 on mounting element 440. The stop or pushing element prevents the retractor element from being inserted too far into the hollow organ.

Expansion element 422 is has a plurality of expansion states, including, for example, an unexpanded state, a fully expanded state, and at least one partially expanded state. As indicated above, the expansion states of expansion element 422 are controlled by sequencing means 430. Expansion element 422 may be any type of expansion element, for example, a balloon. The preferred expansion element shown in the figures is a balloon which, when substantially fully expanded, is in the shape of a circular toroid.

Sequencing means 430 may comprise means for causing the elements to assume the following states, for example, in seriatim:

a) a first state where retractor element 410 is locked in a fully extended position relative to hole forming element 410 with expansion element 422 in the unexpanded state;

b) a second state in which expansion element 422 is in the fully expanded state and expansion element 422 moves toward hole forming element 410;

c) a third state in which the hole has been formed; and d) a fourth state in which expansion element 422 is in the partially expanded state and expansion element 422 is moved to be at least partially disposed in hole forming element 410.

Sequencing means 430 may also include a means for expanding expansion element 422 between the plurality of expansion states. Suitable means for expanding include, for example, a syringe in fluid communication with expansion element 422 or a cylinder having a piston slideable therein and coupled to expansion element 422. Sequencing means 430 may also include a means for moving retractor element 420 relative to hole forming element 410, whereby expansion element 422 is moved from a position distally outside of hole forming element 410 to a position at least partially disposed within hole forming element 410. A sequencing bolt 432 may be coupled to the means for expanding, and may be used to control sequencing means 430.

Prior to the hole being formed in the hollow organ, hemostatic connection assembly 300 is positioned on applicator 400 such that a fluid seal is formed between hemostatic connection assembly 300 and applicator 400. Specifically, hemostatic connection assembly 300 is preferably positioned on mounting element 440 and connected to the hollow organ such that a first fluid seal exists between the wall connection portion 310 and the wall of the hollow organ and a second fluid seal exists between hemostatic connection assembly 300 and applicator 400, thereby minimizing fluid loss from the hollow organ.

In a preferred embodiment, hemostatic connection assembly 300 is placed on applicator 400 after pledgeted sutures have been loosely applied to the hollow organ, leaving enough suture length to allow free movement of hemostatic connection assembly 300 relative to the hollow organ. In an alternative procedure, hemostatic connection assembly 300 may be placed on applicator 400 prior to pledgeted sutures being applied to the hollow organ.

Figure 6:
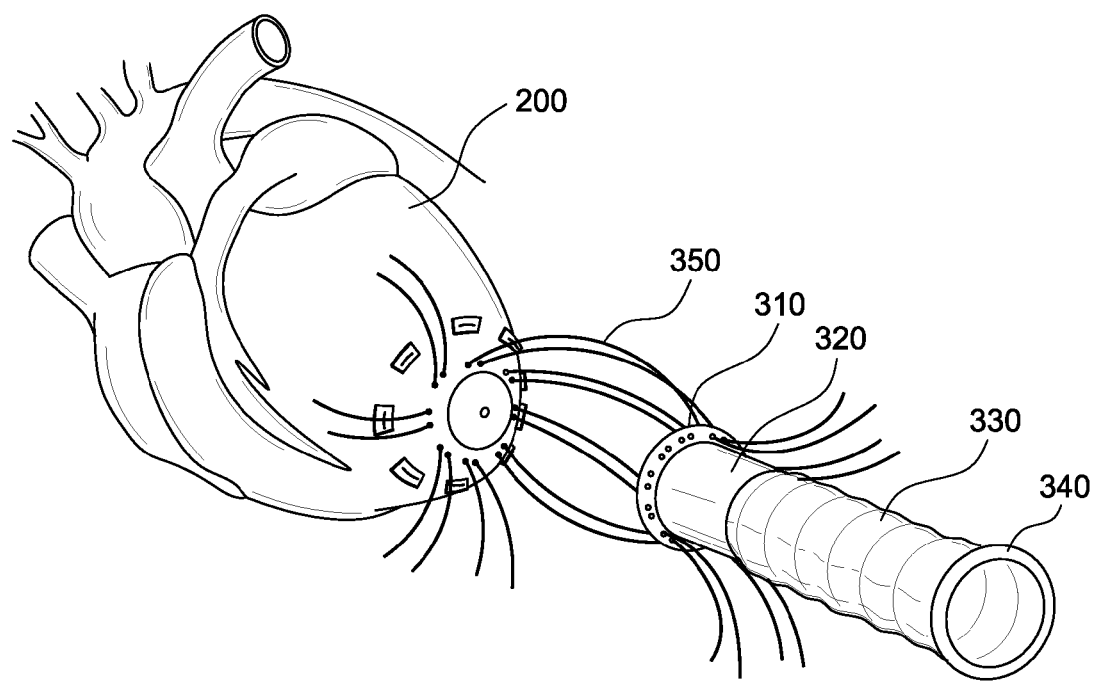
FIG. 6 illustrates an embodiment of the invention in which a hemostatic connection assembly is being connected to a heart using sutures.
Figure 7:
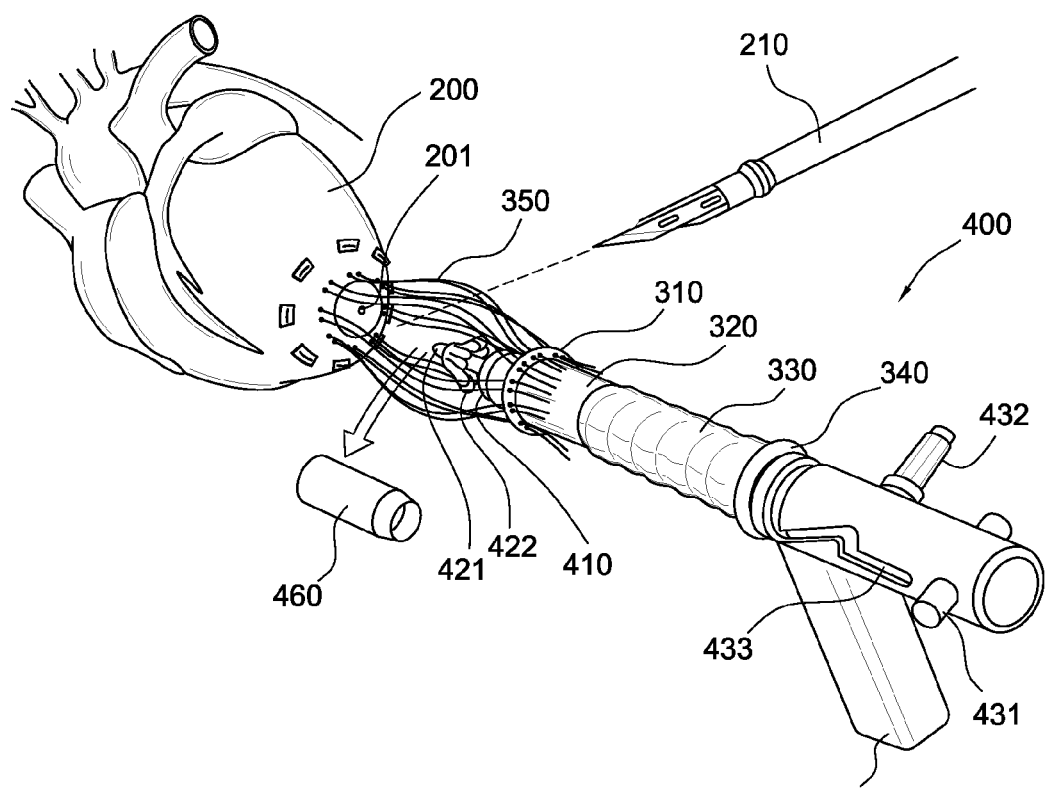
FIG. 7 illustrates an embodiment of the invention in which a hemostatic connection assembly is positioned on an applicator as the hemostatic connection assembly is being connected to a heart using sutures.
Figure 8:
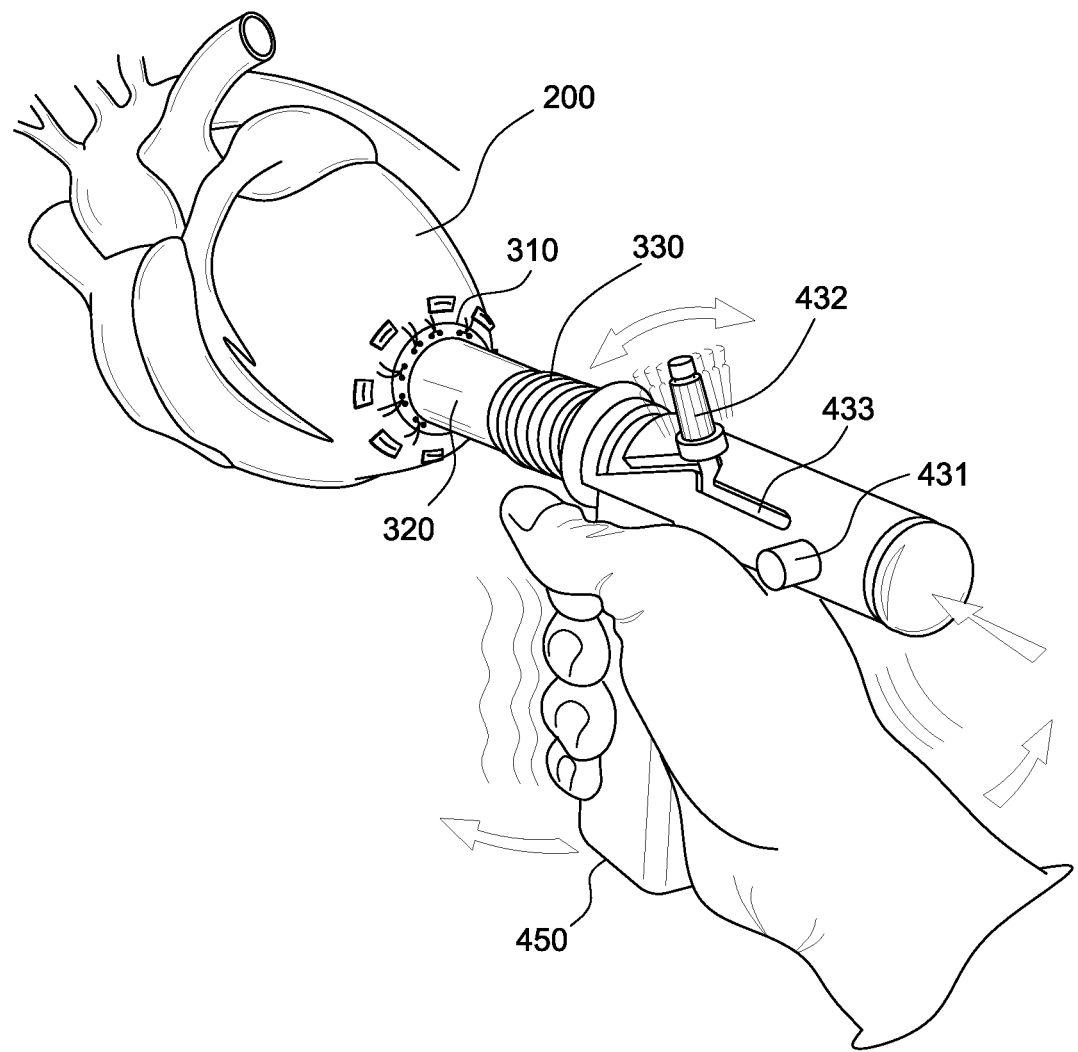
FIG. 8 illustrates an embodiment of the invention in which a hemostatic connection assembly is positioned on an applicator as a hole is being formed in the wall of the heart.

As is shown in FIG. 6, after a position on the hollow organ is selected where the inlet cannula will be located (and a trace line is made on the hollow organ, if needed), hemostatic connection assembly 300 is preferably connected to a wall of the hollow organ 200 such that a fluid seal is formed between hemostatic connection assembly 300 and the wall of hollow organ 200. FIG. 6 illustrates an embodiment of the invention in which hemostatic connection assembly 300 is being connected to hollow organ 200 (in this case, a beating heart) using sutures 350. Preferably, eight to twelve large pledgeted sutures (i.e. mattress sutures) are made around the trace line. Any known means may be used to connect hemostatic connection assembly 300 to a hollow organ 200.

Figure 9:
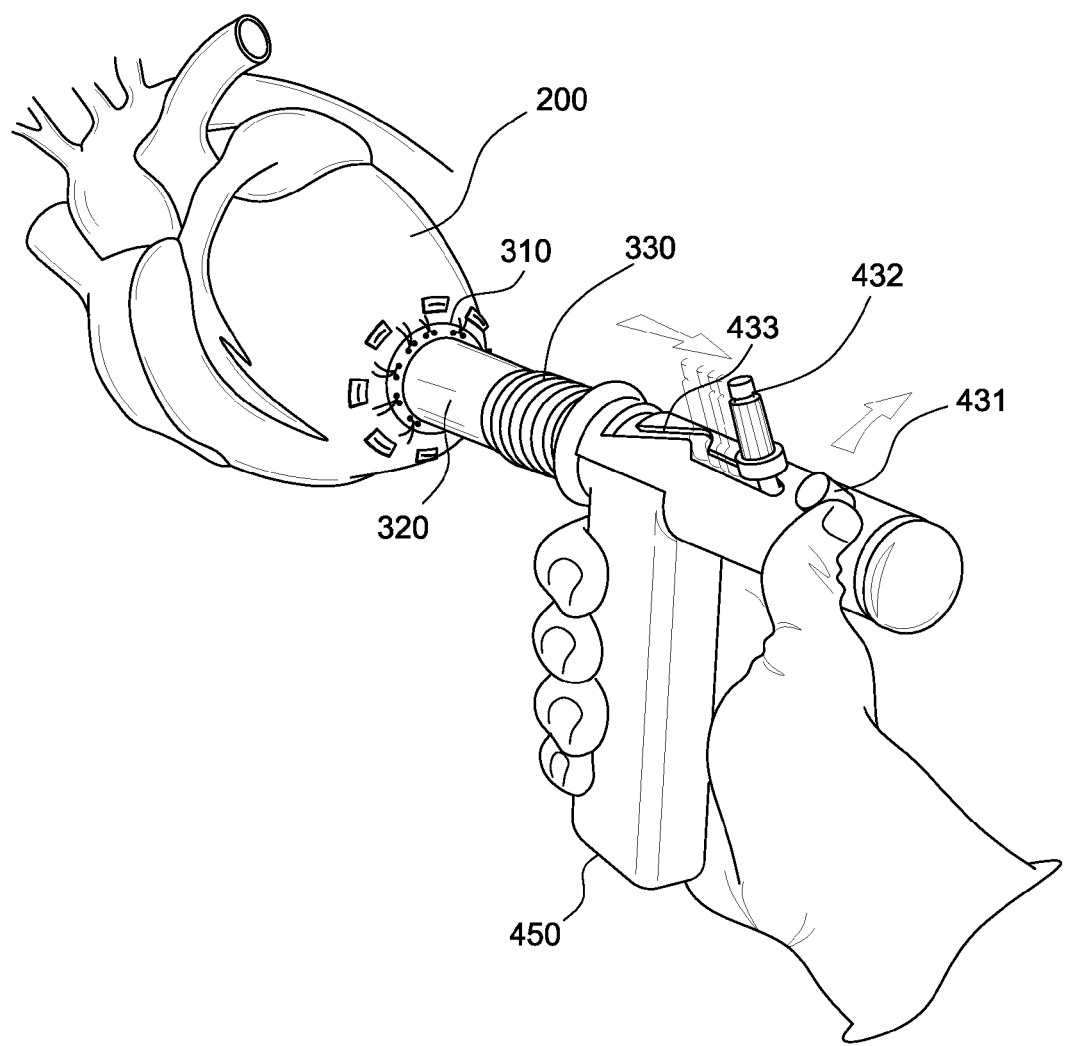
FIG. 9 illustrates an embodiment of the invention in which a hemostatic connection assembly is positioned on an applicator as the sequencing means of the applicator is being operated.

Preferably, wall connection portion 320 is connected to the wall of hollow organ 200. After the connection is initialized, applicator 400 is used to cut a hole in the wall of hollow organ 200. As is shown in FIGS. 6-14, a small starter hole 201 is cut with a sharp instrument 210, such as a scalpel, and a protective cover 460 is removed from applicator 400. (See FIG. 7). The connection between hemostatic connection assembly 300 and the wall of the hollow organ 200 is preferably secured before the tip 421 of retractor element 420 is inserted into starter hole 201. (See FIG. 8). At this point, disk portion 423 of retractor element 420 is firmly positioned against the hollow organ, and deflated expansion element 422 is now within the organ. Sequencing means 430 is used to expand expansion element 422 and partially retract expansion element 422 against the inner wall of hollow organ 200. This sequential state is illustrated by the position of sequencing bolt 432 in sequencing slot 433. The surgeon will then rotate applicator 400 via handle 450 to cause hole forming element 410 to form the hole in the wall of the hollow organ using the applicator. As can be seen in FIG. 9, extension portion 330 is compressed while the hole is being formed. After the hole is formed, the surgeon activates safety latch 431, thereby causing sequencing bolt 423 to finish its movement within slot 433, thereby causing expansion element 422 to enter a partially expanded state, and retracting expansion element 422, and the tissue plug 202, at least partially into hole forming element 410.

Figure 10:
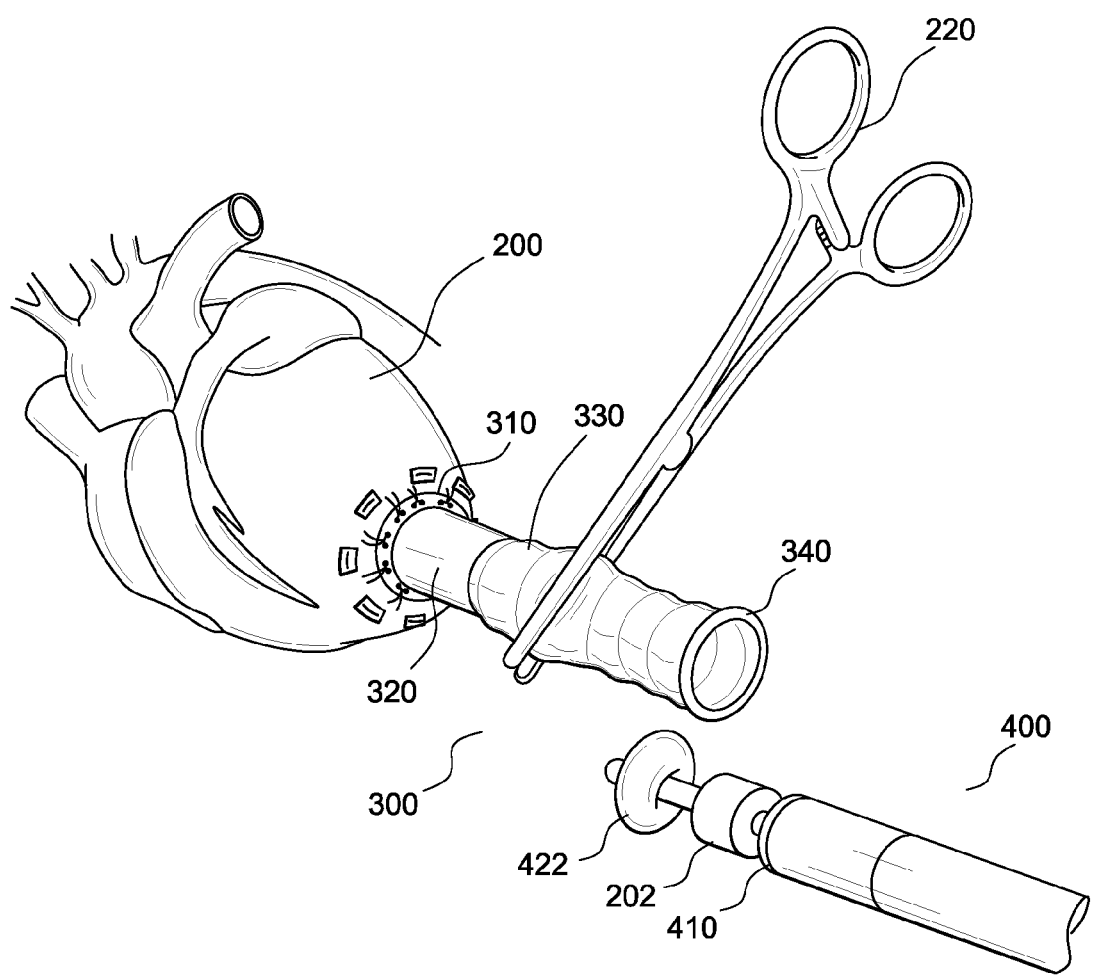
FIG. 10 illustrates an embodiment of the invention in which a hemostatic connection assembly is connected to the heart with the applicator removed.

Applicator 400 is then withdrawn from the hole formed in the wall of hollow organ 200 while maintaining the fluid seal between hemostatic connection assembly 300 and the applicator 400. After applicator 400 is withdrawn, causing extension portion 330 to be extended outwardly from hollow organ 200, hemostatic connection assembly 300 is occluded to form a fluid seal. An exemplary occlusion is a compression of extension portion 330, for example, by clamping with a clamp 200, as is shown in FIG. 10. After this fluid seal is established, applicator 400 is detached from hemostatic connection assembly 300. As can be seen in FIG. 10, a tissue plug 202 is retained on retractor element 420 between expansion element 422 and hole forming element 410. It should be noted that the sequencing bolt has been moved forward within the sequencing slot after withdrawal of the applicator from the hollow to allow exposure of the tissue plug for illustrative purposes.

After applicator 400 is removed from hemostatic connection assembly 300, the tubular portion 510 of an inlet conduit 500 is inserted into hemostatic connection assembly 300 such that a fluid seal is formed between hemostatic connection assembly 300 and inlet conduit 500. During this process, hemostatic connection assembly 300 and inlet conduit 500 should be filled with saline to eliminate entrapped air.

Figure 11:
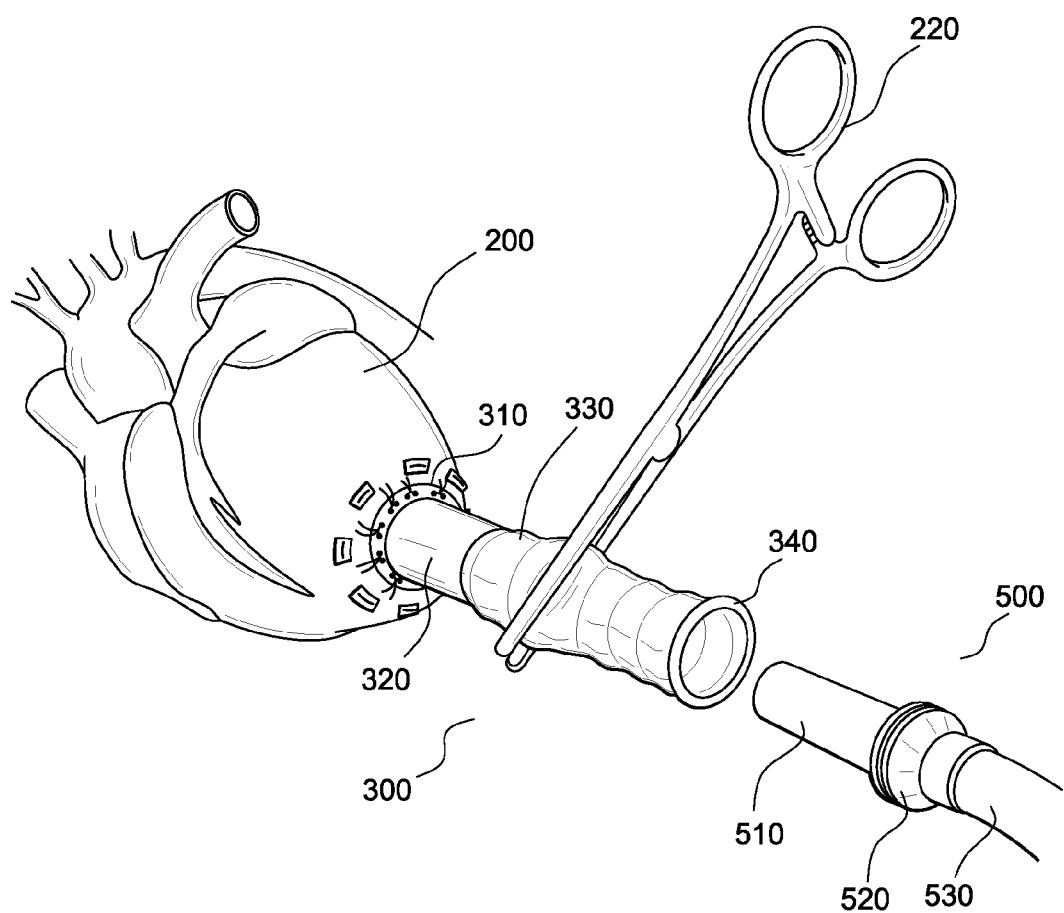
FIG. 11 illustrates an embodiment of the invention in which a hemostatic connection assembly is connected to the heart and an inlet conduit is ready to be inserted.
Figure 12:
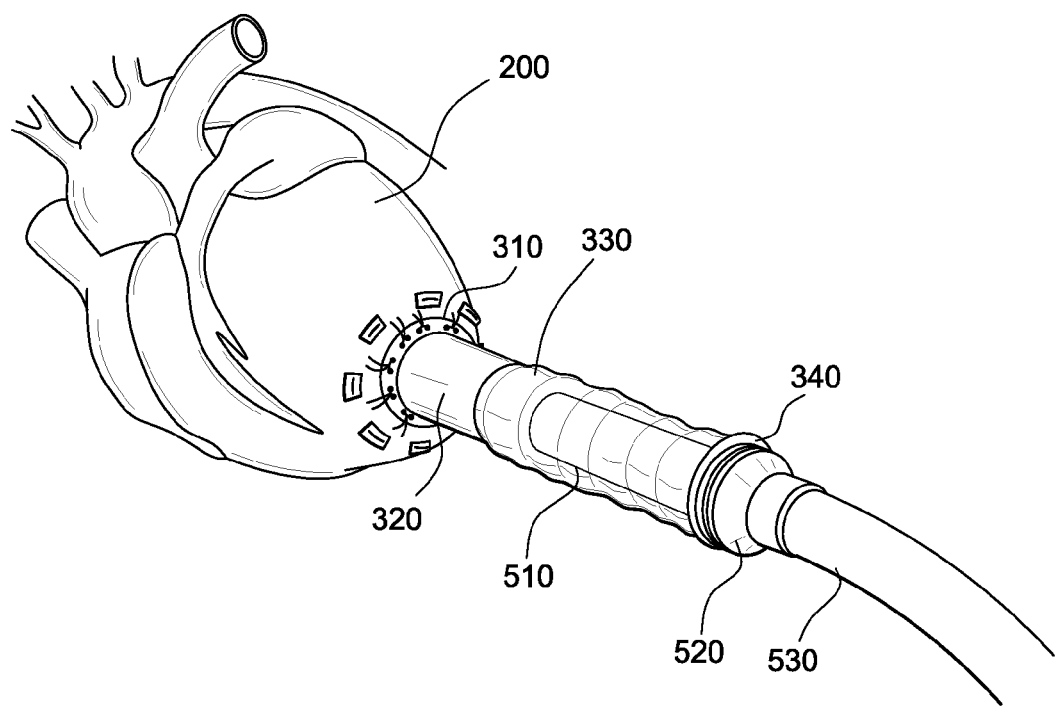
FIG. 12 illustrates an embodiment of the invention in which a hemostatic connection assembly is connected to the heart and an inlet conduit has been partially inserted.

For example, as is shown in FIG. 11-12, the fluid seal may be formed by positioning seal ring portion 340 on a flange portion 520 of inlet conduit 500. The fluid seal may also be formed between hemostatic connection assembly 300 and inlet conduit 500 using sutures or umbilical tape, for example. After this seal is established, the occlusion of hemostatic connection assembly 300 (i.e. clamp 220) is removed.

Figure 13:
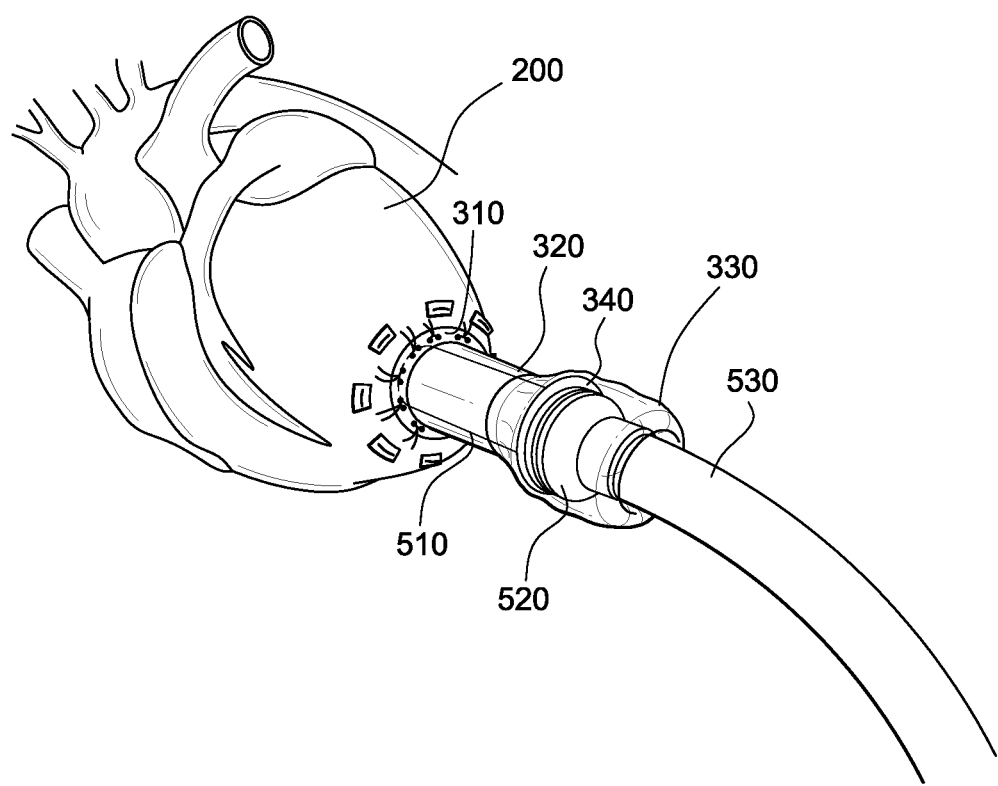
FIG. 13 illustrates an embodiment of the invention in which a hemostatic connection assembly is connected to the heart and an inlet conduit has been fully inserted.
Figure 14:
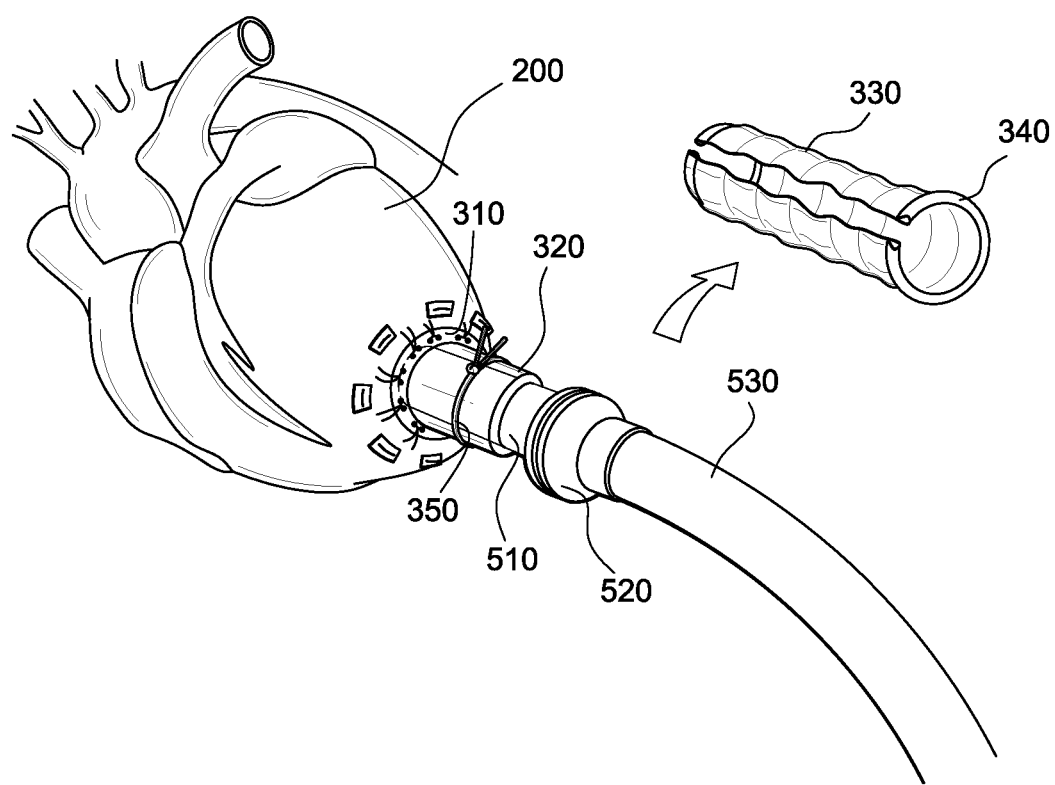
FIG. 14 illustrates an embodiment of the invention in which a hemostatic connection assembly is connected to the heart and an inlet conduit has been fully inserted, and a portion of the hemostatic connection assembly has been removed.

As is shown in FIG. 13, after the occlusion is removed, tubular portion 510 of inlet conduit 500 is inserted into the hole formed in the wall of hollow organ 200. As can be seen in the figures, extension element 330 is essentially folded over in this position.

To finalize the installation, a further fluid seal between inlet conduit 500 and hemostatic connection assembly 300 is formed, for example, by creating a fluid seal between cuff portion 320 and inlet conduit 500 with a long suture 350 or a length of umbilical tape. This both creates a hemostatic seal and sets the position of inlet conduit 500 relative to cuff portion 320. At this point, extension portion 300 and seal ring portion 340 may be removed. Device connection portion 530 of inlet conduit 500 extends to the connected device, such as a valved conduit or LVAD.

Figure 15:
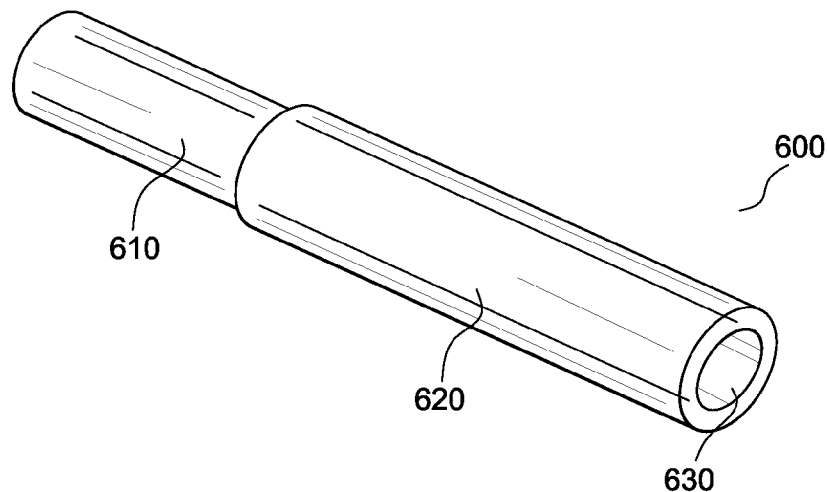
FIG. 15 illustrates an exemplary centering fixture of the invention.
Figure 16:
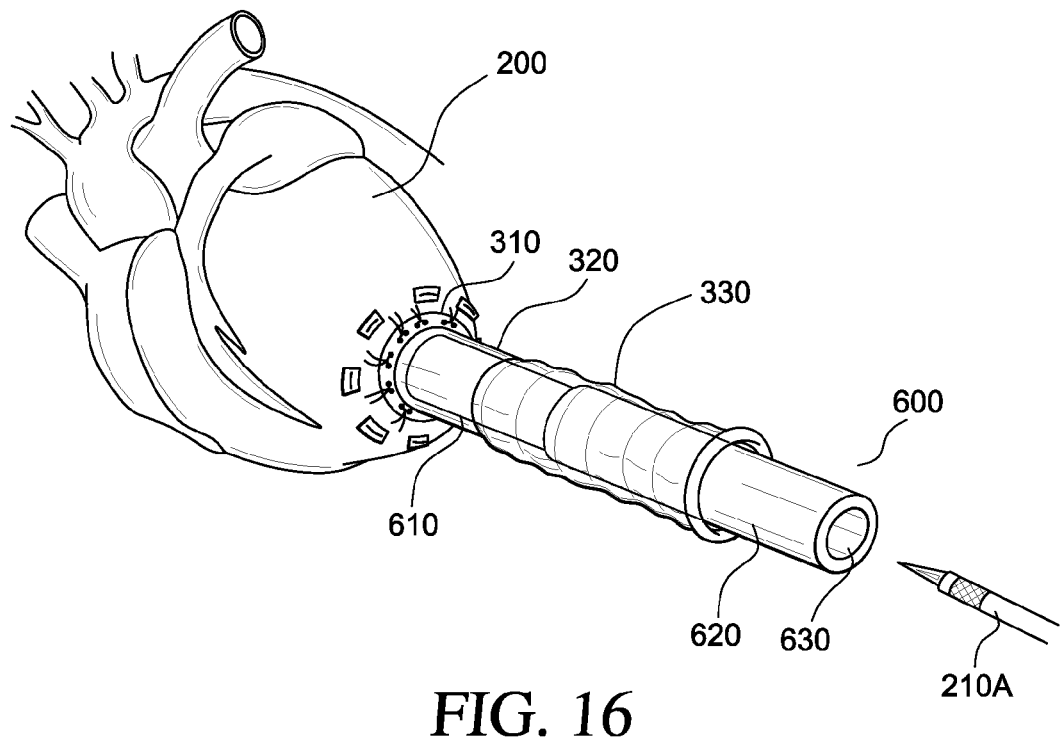
FIG. 16 illustrates an embodiment of the invention in which a hemostatic connection assembly has been connected to a heart, and a centering fixture of the invention is positioned within the hemostatic connection assembly.
Figure 17:
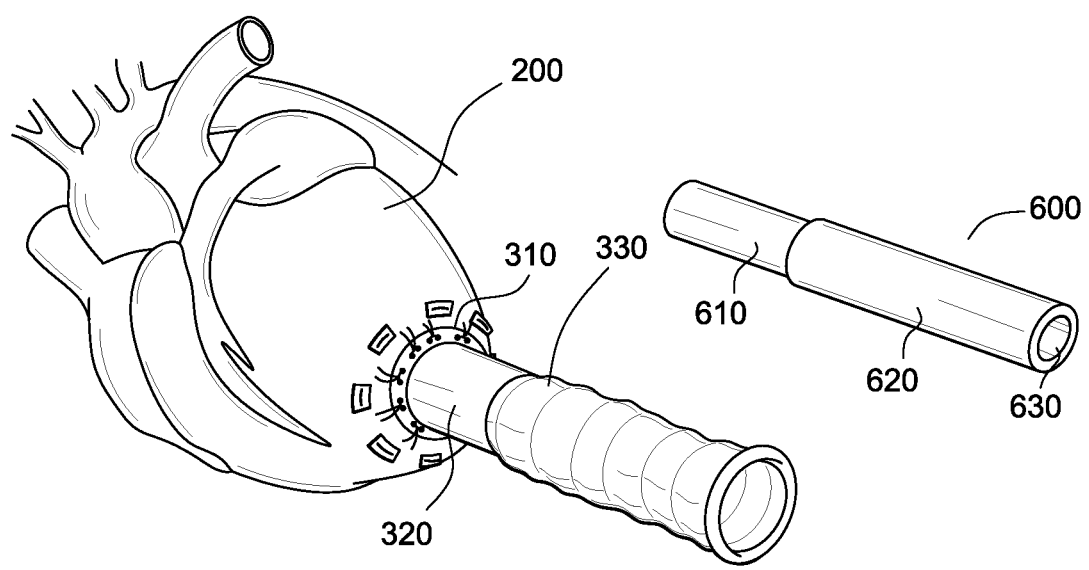
FIG. 17 illustrates an embodiment of the invention in which a hemostatic connection assembly has been connected to a heart, and a centering fixture of the invention has been removed from the hemostatic connection assembly.

FIGS. 15 and 16 illustrate a centering fixture 600 which may be used to center starter hole 201 on hollow organ 200 relative to hemostatic connection assembly 300. Centering fixture 600 has a smaller outer diameter portion 610 that fits snugly within cuff portion 320 of hemostatic connection assembly 300 and a larger outer diameter portion 620 that fits within the extension portion 330 of hemostatic connection assembly 300. If desired, centering fixture 600 may be used to hold hemostatic connection assembly 300 while sutures are being applied. Obviously, centering fixture 600 must be removed before placing hemostatic connection assembly 300 on applicator 400.

Centering fixture 600 may also be used to hold hemostatic connection assembly 300 while wall connection portion 310 is connected to hollow organ 200. In this embodiment, centering fixture 600 allows the surgeon to insert a scalpel 210A or other sharp instrument into centering fixture 600 to make a small stab wound at the apex without risking damage to the inner surface of extension portion 330.

While the above description focuses primarily on attachment of a hemostatic connection assembly, such as a sewing cuff assembly, to a hollow organ, such as a heart, it should be understood that the same devices and procedures will allow attachment of devices with inlet conduits to other hollow organs, for example but not limited to gastrointestinal and urinary organs (i.e. for electrical stimulation and or monitoring of the GI tract), access to the bladder for enhancement of function or treatment of disease such as bladder cancer, implantation of apparatus such as stomach bypass tubes for treatment of morbid obesity or for limiting passage through the pylorus valve, access for implanting augmentation or enhancement devices for closure of body lumens such as magnetic or mechanical sphincters, endoscopic delivery means for diagnosing/treating gastric disorders, delivery of a resident sensing device, therapeutic delivery device, access means for removing tumors from hollow organs, access means for delivering and removing tumor treatment devices (i.e. radiation devices), access means for attaching graft to blood vessels, means of simultaneous cut-and-attach graft, and the like.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

What is claimed is:

1. A system comprising a hemostatic connection assembly and an inlet conduit,
   the hemostatic connection assembly for interconnecting the inlet conduit to a hollow organ, the hemostatic connection assembly comprising:
      an organ wall connection portion adapted for connection to a wall of the hollow organ and to provide a cuff portion extending from the organ;
      the cuff portion being connected to said organ wall connection portion, and the cuff portion being adapted to support the inlet conduit during insertion of the inlet conduit through a wall of the hollow organ;
      an extension portion connected to the cuff portion, said extension portion being movable between a compressed state and an extended state; and
      a seal ring portion mounted on said extension portion, said seal ring portion being adapted to connect to a portion of the inlet conduit,
   the inlet conduit comprising a tubular portion configured to enter said extension portion through said seal ring portion, and a flange portion for engagement with said seal ring portion;
   wherein, during the connecting of the inlet conduit to the hollow organ, a first fluid seal is provided between said organ wall connection portion and the wall of the hollow organ, and a second fluid seal is provided between the hemostatic connection assembly and the inlet conduit, whereby to minimize fluid loss from the hollow organ.

2. The system of claim 1, wherein the inlet conduit comprises an inlet cannula.

3. The system of claim 1, wherein the hollow organ comprises a beating heart.

4. The system of claim 1, wherein said organ wall connection portion of the connection assembly is adapted to be connected to the wall of the hollow organ by sutures.

5. The system of claim 1, wherein said organ wall connection portion of the connection assembly is adapted to be connected to the wall of the hollow organ by adhesive.

6. The system of claim 1, wherein said organ wall connection portion is integral with the cuff portion.

7. The system of claim 1, wherein the cuff portion is integral with said extension portion.

8. The system of claim 1, wherein said extension portion is integral with said seal ring portion.

9. The system of claim 1, wherein said organ wall connection portion, the cuff portion, said extension portion, and said seal ring portion are integrally formed.

10. The system of claim 1, wherein said extension portion is removably connected to the cuff portion.

11. The system of claim 1, wherein the cuff portion is substantially rigid.

12. The system of claim 1, wherein said extension portion is of a flexible material.

13. The system of claim 12, wherein the flexible material is polyurethane.

14. The system of claim 1, wherein said extension portion includes at least one convolution.

* * * * *